United States Patent [19]

Grant et al.

[11] Patent Number: 5,202,130
[45] Date of Patent: Apr. 13, 1993

[54] SUPPRESSION OF ECZEMATOUS DERMATITIS BY CALCIUM TRANSPORT INHIBITION

[75] Inventors: Anhalt Grant, Towson, Md.; Diezel Wolfgang, Berlin, Fed. Rep. of Germany

[73] Assignee: The Johns Hopkins University, Baltimore, Md.

[21] Appl. No.: 400,657

[22] Filed: Aug. 31, 1989

[51] Int. Cl.$^5$ ...................... A61K 33/24; A61K 31/28
[52] U.S. Cl. .................................. 424/617; 514/211; 514/356; 514/492; 514/523; 514/861; 514/887
[58] Field of Search ............................ 424/600, 617, ; 514/211, 356, 523, 828, 861, 887, 492

[56] References Cited

U.S. PATENT DOCUMENTS 4,485,054  11/1984  Mezei et al. .
4,556,560  12/1985  Buckingham ...................... 514/494

FOREIGN PATENT DOCUMENTS 0084898  8/1983  European Pat. Off. .

OTHER PUBLICATIONS

"Suppression of Cutaneous Hypersensitivity" by Lanthanum in clinical research, 37(2) 1989, p. 349A; National meeting of the American Federation for Clinical Research Washington D.C., U.S.A.

"CRC Handbook of Chemistry and Physics" 66th edition 1985–86 p. F-164 Editor—in—Chief R. C. Weast.

Evans, C. H., "Interestin and useful biochemical properties of lanthanides", *Trends in Biochemical Sciences*, 1983, vol. 8, pp. 445–449.

Epstein (1987), in Fitzpatrick, et al., eds., Dermatology in General Medicine, McGraw-Hill, New York, pp. 1373–1383.

Texbook of Dermatology, 4th ed., Rook, et al., eds., Blackwell Scientific Publications, Oxford, 1986, pp. 239–244.

Toews, et al. "Epidermal Langerhans Cell Density Determines Whether Contact Hypesensitivity or Unresponsiveness Follows Skin Painting with DNFB," J. Immunol. (1980), 124:445–453.

Noonan, et al. "Suppression of Contact Hypersensitivity in Mice by Ultraviolet Irradiation is Associated with Defective Antigen Presentation," Immunol. (1981), 43:527–533.

Perry et al., "Antigen Presentation by Epidermal Langerhans Cells: Loss of Function Following Ultraviolet (UV) Irradiation in vivo," Clin. Immunol. Immunopath. (1982), 24:204–219.

Belsito et al, "Effect of Glucocorticosteriods on Epidermal Langerhans Cells," J. Exp. Med. (1982), 155:291–302.

Krueger et al., "Biology of Langerhans Cells: Analysis by Experiments to Deplete Langerhans Cells from Human Skin," J. Invest. Dermatol. (1984), 82:613–617.

Rheins et al., "Modulation of the Population Density of Identifiable Epidermal Langerhans Cells Associated with Enhancement or Suppression of Cutaneous Immune Reactivity," J. Immunol. (1986), 136:867–876.

Miyauchi et al., "Epidermal Langerhans Cells Undergo Mitosis During the Early Recovery Phase After Ultraviolet-B Irradiation," J. Invest. Dermatol. (1987), 88:703–708.

(List continued on next page.)

*Primary Examiner*—Nicholas S. Rizzo
*Assistant Examiner*—Jyothsna Venkat
*Attorney, Agent, or Firm*—Banner, Birch, McKie & Beckett

[57] ABSTRACT

Treatment of an animal with calcium flux inhibitors results in a decrease in the number of epidermal Langerhans cells and a simultaneous decrease in the ability to respond to contact sensitizing agents. Also, topical application of calcium flux inhibitors will reduce inflammation in patients experiencing delayed-type hypersensitivity reaction or atopic eczema. Thus, calcium flux inhibitors represent a new class of therapeutic agents in the treatment of contact dermatitis and eczema.

27 Claims, 2 Drawing Sheets

OTHER PUBLICATIONS tivity by Calcium Transport Inhibitors Lanthanum and Diltiazem," Abstract, Clin. Res. (1988), 36:813A.

Diezel, "Suppression of Cutaneous Contact Hypersensitivity by Lanthanum," Abstract, Clin. Res. (1989)m 37:349A.

Diezel, "Inhibition of Cutaneous Contact Hypersensitivity by Calcium Transport Inhibitors Lanthanum and Diltiazem," J. Invest. Dermatol. (1989), 93:322–326.

Wolff et al., "An Electron Microscopic Study on the Extraneous Coat of Keratinocytes and the Intercellular Space of the Epidermis," J. Invest. Dermatol. (1968), 51:418–430.

Basu et al., "Neurotoxicity of Lanthanum Chloride in Newborn Chicks," Toxicol. Letters (1982), 14:21–25.

Schneider et al., "Secretion of Granule Enzymes from Alveolar Macrophages," Experiment. Cell Res. (1978), 112:249–256.

Onozaki et al., "The Mechanism of Macrophage Activation Induced by $Ca^{2+}$ Ionophore," Cell. Immunol. (1983), 75:242–254.

Morse et al., "Effect of Nifedipine of 67K Calcimedin in Cultured Macrophages and Smooth Muscle Cells," Biochem. Biophys. Res. Comm. (1987), 145:726–732.

Lee et al, "Mechanism of Calcium Channel Blockade by Verapamil, D600, Diltiazem and Nitrendipine in Single Dialysed Heart Cells," Nature (1983), 302:790–794.

Mezei, "Liposomes in the Topical Application of Drugs: a Review," in "Liposomes as Drug Carriers," ed. Gregoriadis, Wiley and Sons, pp. 663–667.

Diezel, "Suppression of Cutaneous Contact Hypersensi-

SUPPRESSION OF ECZEMATOUS DERMATITIS BY CALCIUM TRANSPORT INHIBITION

The U.S. Government has a paid-up license in this invention and the right in limited circumstances to require the patent owner to license others on reasonable terms as provided for by the terms of Grants number R1AR32490 and KO4AR016868 awarded by the National Institutes of Health.

FIELD OF THE INVENTION

This invention concerns calcium flux inhibitors which represent a novel class of therapeutic agents in the treatment of contact dermatitis and eczema.

BACKGROUND OF THE INVENTION

Eczematous dermatitis is a characteristic inflammatory response of the skin due to both endogenous and exogenous factors. Eczematous dermatitis is sufficiently serious to account for the highest incidence of skin disease, being response for incalculable loss of time and productivity in industry. Approximately one-third of all patients in the United States seen by dermatologists have eczema.

In particular, classic delayed-type hypersensitivity and allergic contact dermatitis represent common clinical problems. The potential contact sensitizing antigens to which humans are exposed are multitudinous and include drugs, dyes, plant oleo resins, preservatives, and metals. The five most common contact sensitizing agents encountered in clinical practice are Rhus species of plants (poison ivy, oak, or sumac), paraphenylenediamine, nickel compounds, rubber compounds, and the dichromates. They can lead to delayed hypersensitivity responses, which may represent significant medical problems. Thus a great deal of study has focused on pharmacological ways to modulate this type of immune response.

Delayed-type hypersensitivity (DTH) is a T-cell dependent immune phenomenon manifested by an inflammatory reaction at the site of antigen deposition, usually the skin, that reaches its peak intensity 24 to 48 hours after challenge by the antigen. Contact sensitivity (CS), a form of DTH, is observed by sensitizing animals to antigen through cutaneous exposure to highly chemically reactive compounds such as trinitrochlorobenzene (TNCB) or dinitrofluorobenzene (DNFB). Animals are subsequently challenged on the skin or on the pinna of one ear 4 to 7 days after sensitization with the contact sensitizer (allergen), and an inflammatory response is observed 24 to 48 hours after challenge. In mice, antigen can be deposited in the pinna or on the foot pad and the swelling determined with callipers or an engineer's micrometer. Swelling in mice sensitized with irrevelant antigen and challenged in the foot pad with the same antigen as the experimental group provides the control for non-specific swelling.

The immune lymphocytes mediating DTH probably encounter antigen at or close to the site of antigen deposition. Studies indicate that Ia-bearing Antibody Presenting Cells take up antigen and "present" it to T-cell precursors to prime them resulting in sensitization. In sensitized animals challenged with allergen, a similar interaction seems to occur between antigen-bearing Antibody Presenting Cells and primed T-cells in order to activate the T-cells. After activation, T-cells secrete a number of lymphokines responsible for attracting mononuclear cells to the inflammatory site and activating them to evolve non-specific tissue destruction. In the case of contact allergic dermatitis, the Antigen Presenting Cell function is apparently supplied by epidermal Langerhans cells.

The simplest treatment of allergic contact dermatitis is avoidance of exposure to an identified allergen, but avoiding known allergens may prove difficult. For example, common sensitizers such benzocaine are employed in a variety of topical medications such as sunburn preparations and antiseptic creams. Unwitting exposure to a known allergen such as poison ivy can occur through contact with the smoke of burning leaves. In addition, the patient may exacerbate an allergic contact dermatitis by exposure to cross-reacting chemical compounds that are similar to the allergen by which the patient was originally sensitized.

Symptomatic treatment usually consists of the application of topical corticosteroids. Prolonged topical use of corticosteriods can produce undesirable side effects such as atrophy of the skin and systemic absorption of the corticosteriods. Oral or parenteral corticosteriods may be needed temporarily in severe cases, but long term therapy with exogenous corticosteriods can produce Cushing's syndrome. The decreased DTH seen in mammals exposed to steroids might be due to the lympholytic function of these agents. In addition it has recently been observed that glucocorticosteriods applied topically or administered systemically seem to lead to a decrease in the density of epidermal Langerhans cells, which are critically important in the presentation of antigen in contact sensitivity.

Another potential approach to treatment of DTH involves systemically depleting Antigen Presenting Cells by ultraviolet radiation. It has been shown in vivo exposure of mice to UV irradiation leads to impaired antigen presentation by Antigen Presenting Cells and to a systemic decrease in the number of Ia-bearing Antigen Presenting Cells. Many Ia-bearing Langerhans cells, which are known to be important in the presentation of skin contactants to immune T-cells, also disappear from the skin. When such UV-irradiated mice are contact sensitized or immunized subcutaneously with hapten-coupled cells, they are not primed for DTH responses; instead they develop antigen-specific suppressor T-cells. Thus one can selectively modulate activation of T-cells by preventing presentation of ligand by Antigen Presenting Cells. It has not been proven that an identical phenomenon occurs in human beings exposed to UV irradiation.

SUMMARY OF THE INVENTION

It is an objective of this invention to provide a new treatment for allergic contact dermatitis. It is another object of this invention to provide a treatment method which prevents the development of delayed-typed hypersensitivity to particular contact allergens. It is a further object of this invention to provide a new treatment method that prevents the development of inflammatory reactions in the skin of animals, especially humans, challenged with an allergen to which they have previously developed sensitivity. It is the further object of this invention to provide a new treatment method that reduces inflammatory reactions in the skin of humans that suffer from endogenous (atopic) dermatitis. These and other objects can be met by the following embodiments of this invention.

This invention contemplates a method for the suppression of allergic contact sensitization in an animal (e.g. mammals including humans) comprising administering a therapeutically effective amount of a calcium flux inhibiting compound to the animal. This invention further contemplates a method for the treatment of eczematous dermatitis comprising administering to an animal a therapeutically effective amount of a calcium flux inhibiting compound by topical application. In particular, this invention contemplates methods to treat allergic contact dermatitis by preventing sensitization or by suppressing inflammation in sensitized individuals upon challenge by the allergen comprising administering to the individual a calcium flux inhibiting compound in pharmaceutical compositions, especially those designed for topical application.

In one aspect, this invention provides a method for treating eczematous inflammation, especially inflammation due to atopic eczema, comprising topical application of a calcium flux inhibitor in an amount sufficient to reduce the inflammation. In another aspect, the invention provides a method for the treatment of contact allergic dermatitis comprising administering a therapeutically effective amount of a calcium flux inhibiting compound. In particular embodiments, this alternative aspect of the invention provides a method to suppress sensitization to a contact sensitizing agent comprising administering a calcium flux inhibiting compound prior to exposure of the individual to the contact sensitizing agent and a method for treating inflammation resulting from exposure to a contact sensitizing agent comprising administering a calcium flux inhibitor to an individual who has been sensitized to said agent. This invention further provides pharmaceutical compositions for the treatment of allergic contact dermatitis or eczematous inflammation comprising a therapeutically effective amount of a calcium flux inhibitor and a carrier that is pharmaceutically acceptable for topical application.

It has been discovered that treatment of an animal with an effective amount of calcium flux inhibitors results in a decrease in the number of epidermal Langerhans cells. Simultaneously with the loss of the epidermal Langerhans cells, the animal loses the ability to respond to contact sensitizing agents. This loss of response to contact sensitizing agents has been shown to be due to the generation of antigen-specific suppression mediated by T-cells. It has also been discovered that administration of calcium flux inhibitors will reduce inflammation in patients experiencing DTH reaction. It has further been discovered that administration of calcium flux inhibitors to humans suffering from atopic dermatitis affecting the hands will reduce inflammation when these individuals expose themselves to irritants or sensitizing agents in their environment. Thus calcium flux inhibitors represent a new class of therapeutic agents, effective against contact dermatitis and eczema without the particular side effects associated with the existing therapies. Therefore they provide needed alternative means for treating this disease.

DETAILED DESCRIPTION OF THE INVENTION

Macrophages have been shown to have calcium dependent membrane potentials which may be mediated by calcium-ATPase on their surfaces. Calcium has been shown to be involved in metabolism and inhibition of motility of macrophages, and the secretion of granule enzymes can be simulated by calcium ion. However the antigen presenting function of macrophages has not been previously associated with calcium-dependent effects.

The present inventors have discovered that treatment with calcium flux inhibitors results in a decrease in the number of epidermal Langerhans cells, skin cells which perform the allergen presenting function in the case of allergic contact dermatitis. Treatment with calcium flux inhibitors interferes with the initial steps in the priming reaction or in activating of T-cells after sensitization of the individual. Thus, in one embodiment, the present invention contemplates the use of calcium flux inhibitors in the treatment of dermatitis resulting from delayed-type hypersensitivity responses.

The calcium flux inhibitors contemplated by this invention can be either organic or inorganic. Organic calcium flux inhibitors bind to and affect the transmembrane calcium channel; inorganic calcium flux inhibitors are analogs of calcium which vary in the reversibility of their binding to calcium binding sites. Of particular interest as an inorganic channel blocker or flux inhibitor is lanthanum, as well as the other lanthanides which behave as calcium analogs. Lanthanides in the 3+ oxidation state have ionic radii near that of calcium, so they fit into calcium binding sites. With their higher charge, they tend to remain bound to calcium binding sites, preventing further activity by calcium-dependent systems. Organic calcium flux inhibitors are currently being used therapeutically as coronary vasodilators (e.g., diltiazem, nifedipine, verampamil) or antiarrythmics (e.g., verampamil). Inorganic calcium flux inhibitors have been used by researchers to explore the effects of calcium transport on cellular metabolism, but have not been used therapeutically (except for cerium which has been reported to be antiemetic in the oxalate salt form).

Studies on lanthanides have shown that they are preferentially accumulated in the skin. Therefore lanthanides administered orally, parenterally or topically will be concentrated in the skin, near the site of therapeutic effectiveness so far as this invention is concerned.

As contemplated by this invention, the calcium flux inhibitors may be formulated with any pharmaceutically acceptable diluent to prepare therapeutically effective compositions for topical application. Examples of such diluents include any of the following bases: hydrophilic ointment USP, emulsion ointment base (water in oil) USP, hydrophilic petrolatum USP, hydrous wool fat-lanolin USP, white wax-bleached bees wax USP, glycerin, water/propylene glycol 50%/50%, and a pure aqueous solution. Optionally, the composition may include additional materials to enhance penetration of the calcium flux inhibitor into the skin. As contemplated by this invention, the penetration enhancing material would promote penetration of the calcium flux inhibitor into the skin. For example, a composition comprising liposomes can accomplish this, as taught in U.S. Pat. No. 4,485,054 and European Patent Application 0,084,898, and reviewed by Mezer in Gregoriadis, ed., "Liposomes as Drug Carriers,"60 John Wiley and Sons, 1988, pp. 663–677. The compositions contemplated by this invention may, of course, include other components, so long as these components do not negate the therapeutic effect of the calcium flux inhibitors.

Formulations containing elements in the lanthanide series will vary, depending on which salt is employed. For example, the chloride salts of lanthanides are soluble in aqueous solution at pH 6.8–7.4. A suitable buffer to maintain the pH in the range of 7.4 would be tris (trishydroxymethylammniomethane) at a concentration of 0.01M. The solubilized chloride salts of lanthanides can then be incorporated into the composition. The chloride salts of lanthanides should be incorporated into the formulation in a therapeutically effective amount, for example at from about 0.001% to about 30% by weight, preferably from about 0.01% to about 20% and most preferably from about 0.01% to about 10%. Other salts, such as the citrate salts of the lanthanides series do not require buffering to physiologic pH. Therefore, they can be incorporated in any of the above preparations at the stated concentrations, and in the absence of any physiologic buffering.

Organic calcium flux inhibitors are formulated in any of the bases provided for inorganic calcium flux inhibitors. The concentration of organic calcium flux inhibitors in the composition should be the same as that used for the inorganics. In addition, the compositions containing organic calcium flux inhibitors preferably also include a penetration enhancing material to promote penetration into the skin.

This invention provides a method of treating allergic contact dermatitis comprising administering a therapeutically effective amount of a calcium flux inhibiting compound to an animal. Allergic contact dermatitis can be suppressed by systemic administration of either organic or inorganic calcium flux inhibiting compounds. However, since these compounds may have toxic effects at levels comparable to their therapeutic levels for suppression of dermatitis, the preferred therapeutic mode for treatment of skin diseases is topical application.

Organic calcium flux inhibitors formulated in an appropriate carrier vehicle will penetrate the skin tissue at least to the level at which the epidermal Langerhans cells are found. Inorganic channel blockers, formulated as described above, will penetrate the epidermis and will be concentrated in that layer. Thus the danger of systemic toxicity is reduced and the therapeutic index is expanded through the topical mode of administration.

This invention contemplates two therapeutic modalities for treatment of allergic contact dermatitis; administration of calcium flux inhibitors to individual prior to sensitization to prevent sensitization to contact allergic agents, and administration to sensitized individuals to avoid activation of T-cells resulting in inflammation following exposure to that contact allergen to which the individual is sensitive (challenge). Preferred treatment protocols are as follows.

1) For prevention of development of contact sensitization. This can be effected by topical application of the chloride salts of elements of the lanthanides series, most preferably in concentrations of from about 0.1% to about 10%, formulated in hydrophilic ointment USP with 0.01M tris HCl, pH 7.0±0.2. The ointment is applied in a thin film twice daily to areas of skin that will be exposed to the suspect allergen. Skin is pretreated prior to exposure, preferably for three days, and continuously during periods of exposure thereafter, preferably on a twice daily basis.

2) For suppression of inflammation due to contact allergens to which individuals are already sensitized, the individual should apply a thin film of the composition described in the preceding paragraph 1 to 6 times daily, preferably 2 to 4 times daily, particularly during exposure to the contact sensitizer.

This invention also provides a method for treating eczematous dermatitis which is not the result of contact sensitization. Lanthanide salts formulated in a suitable diluent for topical application at a therapeutically effective concentration, for example from about 0.001% to about 30%, preferably from about 0.01% to about 20%, most preferably from about 0.1% to about 10%, of the final formulation on a weight basis, are applied to the inflamed skin in a thin film from 1 to 4 times daily.

The following examples are included to further illustrate the invention. They are not intended to limit the scope of the invention as described above or to exclude those modifications in the formulations or treatment methods which will readily occur to those of ordinary skill in the art.

EXAMPLE 1

Effect of systemic $La^{3+}$ on sensitization against DNCB.

Four to six-week-old male BALB/c mice originally obtained from the Jackson Laboratories, Bar Harbor, Me., were bred and maintained in our laboratories. Each experimental group consisted of four mice. Lanthanum chloride ($LaCl_3 \times H_2O$, Morton Thiokol, Inc., Danvers, Mass.) was dissolved in 0.9% NaCl solution. Equimolar amounts of sodium citrate (Sigma Chemical Co., St. Louis, Mo.) were added to obtain lanthanum citrate ($La^{3+}$ citrate). $La^{3+}$ citrate is soluble at pH 7.3 (adjusted with NaOH) and is accumulated in the skin following intraperitoneal administration.

Mice were treated on five consecutive days by intraperitoneal administration of 0.25 mg $La^{3+}$ citrate ($LD_{50}$:78 mg/Kg). Control animals received 0.9% NaCl solution only. On Days 6 and 7 mice were sensitized by applying 25 microliters of 1.0% 1-chloro-2,4-dinitrobenzene (DNCB) (Sigma Chemical Co., St. Louis, Mo.) in a 4:1 acetone:olive oil mixture to the shaved dorsal back surface. Five days later, a challenge dose of microliters of 0.5% DNCB was applied to the dorsal surface of the ear. Ear thickness was measured with an engineer's micrometer (Peacock Inc., Tokyo, Japan) at 24 hours, 48 hours and 72 hours after the challenge and calculated by subtracting pre-challenge values from post-challenge values.

Figure 1:
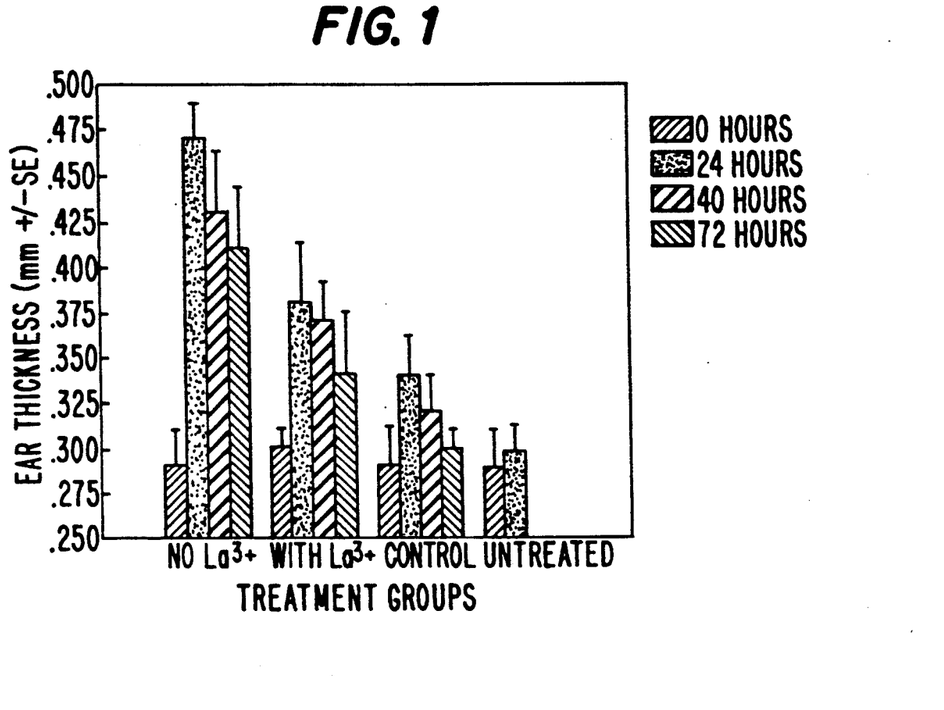
FIG. 1. Decreased sensitization of BALB/c mice against DNCB after systemically administered $La^{+++}$. Lanthanum treatment produced a 56% reduction in ear swelling at 24 h ($p<0.01$) and a 67% reduction at 72 h. Control animals were challenged with DNCB but not sensitized, therefore, the ear swelling in this group reflects irritation by the chemical only.

Systemic $La^{3+}$ produced a 50% reduction in contact hypersensitivity response. Twenty-four hours after the DNCB challenge, mice pretreated systemically with La$^{3+}$ demonstrated ear swelling of 0.08±0.03 mm vs. 0.18±0.02 mm swelling in controls (controls were sensitized and challenged with DNCB but pretreated only with intraperitoneal saline) (p=0.028) (FIG. 1). By 72 hours post-DNCB challenge, the ear thickness in La$^{3+}$-treated animals had returned to near pre-challenge values (pre- vs. post-challenge thickness, 0.29±0.02 mm vs. 0.34±0.03 mm. In contrast, the non La$^{3+}$-treated control mice demonstrated a persistent dermatitis at 72 hours (pre- vs. post-challenge thickness, 0.29±0.02 mm vs. 0.41±0.03 mm) (p=0.028). Negative control mice (that received DNCB without prior sensitization) demonstrated a small increase in ear swelling after 24 hours (0.05±0.02 mm), attributable to the irritant effect of the chemical, and this had returned to near pretreatment levels after 72 hours (0.01±0.01 mm).

EXAMPLE 2

Effect of Systemic La$^{3+}$ citrate on cutaoneous Langerhans cells: ATPase and Ia Staining Mice were treated with systemic La$^{3+}$ citrate as described in Example 1. On day 6, the ear epidermis was obtained from animals treated systemically with La$^{3+}$ citrate and ELC (epidermal Langerhans cell) density and morphology were determined by both ATPase and by Ia staining. Mice were sacrificed by cervical dislocation and their ears were amputated at the base. The skin was separated from underlying cartilage by dissection and pressed dermal side up onto an adhesive surface of a double stick tape (Dermotome Tape, 3M, St. Paul, Minn.), that had previously been fixed onto a glass slide. Ear skin samples on slides were then incubated with 0.02M ethylenediaminetetraacetic acid (EDTA) in PBS for 1.5 hours at 37° C. (25,26), then the epidermis was separated as an intact sheet from the underlying dermis.

Epidermal sheets were stained for ATPase activity according to MacKenzie and Squier (27). Briefly, epidermal sheets were fixed in Tris-maleic acid buffered 4% paraformaldehyde, pH 7.3, for 20 minutes at 4° C. After three washes with a 0.9% NaCl solution, the epidermal sheets were incubated at pH 7.3 in a solution containing 10 mg ATP, 5 ml of 10% MgSO$_4$, 3 ml of 2% Pb(NO$_3$), and 42 ml Tris-maleic acid buffer for one hour at 37° C., washed with 0.9% NaCl solution, and reacted with 0.1% ammonium sulfide for five minutes at room temperature. The stained specimens were mounted in a 9:1 mixture of PBS/glycerol.

Ia-positive cells were stained as follows: EDTA separated epidermal specimens, washed in PBS for 30 minutes, were fixed in cold acetone (−20° C.) for 20 minutes. After washing with PBS, the epidermal sheets were incubated with a 1:100 dilution of anti-mouse I-A$^d$ monoclonal antibody (Becton Dickinson, Mountain View, Calif.) at 4° C. overnight (28). Subsequently, specimens were washed in PBS for two hours and exposed to fluorescein conjugated F(ab')$_2$ fragment goat anti-mouse IgG (Organon Teknika Corp., West Chester, Pa.) at a 1:50 dilution for two hours at 37° C. The epidermal sheets were mounted in Perma Fluor (Lipshaw, Detroit, Mich.).

Slides were coded and read in a "blinded" manner. The density of ELC within each epidermal sheet was determined by using a dual epifluorescent and light microscope (Olympus BH-2, Japan) with a calibrated net micrometer grid. ATPase-positive ELC and Ia-positive ELC present in a 0.25 mm$^2$ area were counted in two random fields per sheet (total: 16 fields per experimental group). ELC density was recorded as the number of cells per mm$^2$ (mean ±S.E.). Statistical significance of the differences between treatment and control groups was calculated using a two-tailed Wilcoxon Rank Sum Test. Differences between groups were considered significant at p=0.05.

La$^{3+}$ citrate administered intraperitoneally for five days at a dosage of 0.25 mg per animal induced a small decrease in Langerhans cell density ion the epidermis of BALB/c mice as determined by both histochemical (ATPase) or immunofluorescent (Ia antigen) methods (Table 1). The density of ATPase positive cells decreased by 13% (based on La$^{3+}$-treated animals/control animals) (p 0.05 ), and the number of Ia-positive cells decreased by 14% (p 0.05).

Furthermore, there were alterations in the morphology of ELC in La$^{3+}$ treated animals, demonstrated by both ATPase and Ia staining. In focal areas, approximately 20% of ELC in La$^{3+}$-treated animals were "rounded up" and without dendrites. Furthermore, the "round" cells were more darkly stained by the ATPase technique (subjectively measured by a darkening of the cell body).

TABLE I

Density of Langerhans cells in ear skin (cells/mm$^2$ ± S.E.) of BALB/c mice pretreated systemically with La$^{3+}$ citrate or with NaCl solution only.

| Type of Pre-treatment | ATPase | Ia |
| --- | --- | --- |
| None | 810 ± 43 | N.E. |
| 0.9% NaCl only | 807 ± 55 | 830 ± 46 |
| La$^{3+}$ citrate | 702 ± 49 | 715 ± 59 |

The decrease in Langerhans cell density (detected by both ATPase staining and Ia staining) was significant, p 0.05. N.E.=not estimated.

EXAMPLE 3

Effect of topically administered La$^{3+}$ on sensitization against DNCB

Mice were treated with 50 microliters of 10% La$^{3+}$ chloride mixture (500 mg La$^{3+}$ chloride dissolved in 5 ml of 95% ethanol:glycerin [4:1 ratio]) applied for five consecutive days to the shaved back surface. Control animals were treated with the ethanol:glycerin vehicle only. On days 6 and 7, 25 microliters of 1.0% DNCB solution was applied to the shaved dorsal back surface. In mice pretreated with topical La$^{3+}$, DNCB was applied only to the shaved dorsal skin that had previously been treated with La$^{3+}$. Five days layer (day 12), the challenge dose of DNCB was applied to the dorsal surface of the ear, and the degree of the ear swelling was determined on day 13.

Figure 2:
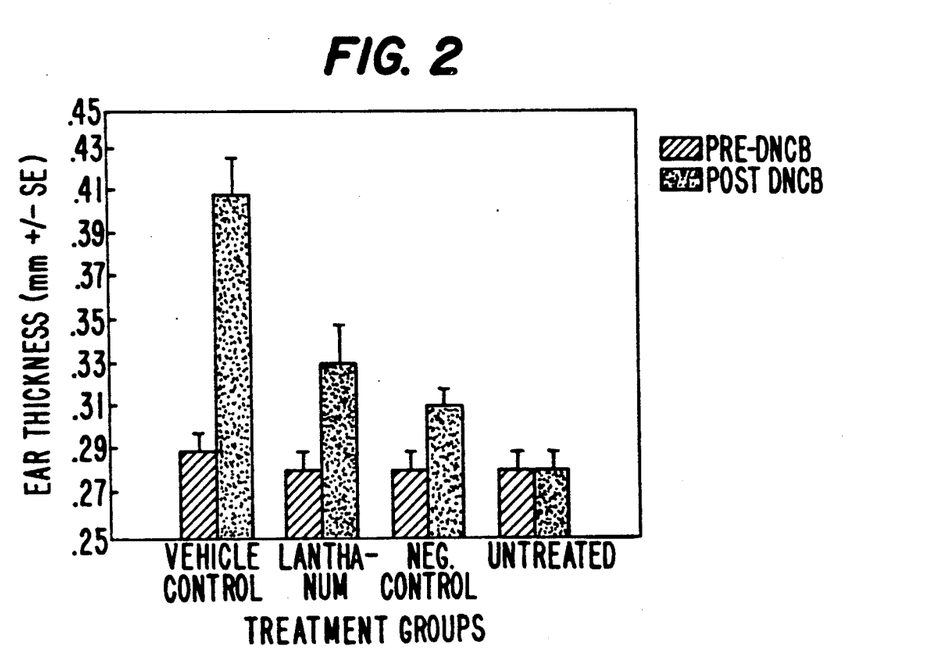
FIG. 2. Decreased sensitization of BALB/c mice against DNCB after topical application of $La^{+++}$ in the area to be sensitized (back skin). DNCB challenge with 25 $\mu$l of 0.25% DNCB was on untreated ear skin. The decrease in ear thickness 24 h post-challenge was 58% (topical $La^{+++}$-treated animals vs. non-$La^{+++}$-treated animals, $p<0.01$). Negative control animals were challenged but not sensitized with DNCB.

Topical La$^{3+}$ produced a 58% reduction in the contact hypersensitivity response. Twenty-four hours after the DNCB challenge, mice pretreated topically with La$^{3+}$ demonstrated swelling of 0.05±0.02 mm vs. 0.12 mm±0.02 mm swelling in controls (p=0.028) (FIG. 2). Negative control mice (challenged with DNCB without prior sensitization) showed ear swelling of 0.03±0.01 mm. The difference in ear swelling between those animals pretreated with topical La$^{3+}$ and the control animals was not statistically significant.

EXAMPLE 4

Inhibition of sensitization of diltiazem

Diltiazem HCl (1,5-Benzothiazepin-4(5H)one, 3-acetoy lox-5-(2-(dimethylamine)ethyl)-2, 3-dihydro-2(4-methoxyphenyl)-, monohydrochloride, (+)-cis) was injected intraperitoneally in a dose of 30 mg/kg ($LD_{50}$=60 mg per kg) two times a day for three days. Two hours after the first injection, mice were sensitized by applying DNCB to the shaved dorsal back skin. Contact sensitization against DNCB was determined five days later.

Figure 3:
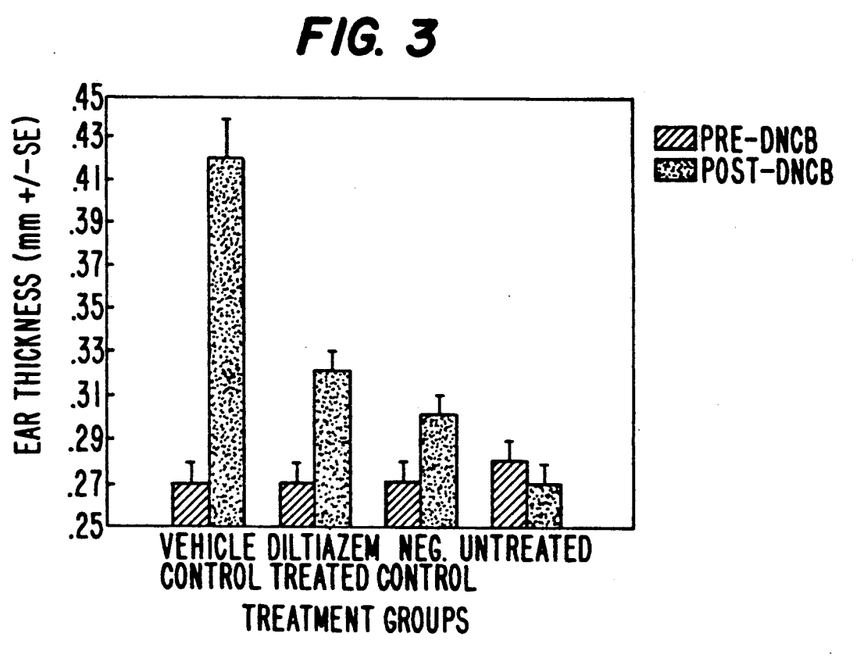
FIG. 3. Decreased sensitization against DNCB after systemic administration of diltiazem during sensitization. Decrease in ear thickness 24 h. post-challenge was 67% (diltiazem-treated animals vs. animals treated with the solvent only, $p<0.001$). Again, negative control animals were challenged but not sensitized with DNCB.

Systemic diltiazem produced a 67% reduction in the contact hypersensitivity response. Mice treated with diltiazem exhibited ear swelling of 0.05±0.01 mm vs. 0.15±0.02 mm in vehicle control animals (vehicle controls were sensitized with DNCB but treated with intraperitoncal injections of vehicle only—FIG. 3). This reduction of ear swelling was highly significant (p=0.001). Animals challenged but not sensitized to DNCB (negative controls) demonstrated ear swelling of only 0.03±0.01 mm. The difference in ear swelling between animals pretreated with diltiazem and the control mice was not statistically significant.

EXAMPLE 5

Prevention of inflammatory reaction by topical $La^{3+}$

In this example, a patient with known allergy against for formaldehyde was challenged with formaldehyde in the presence of lanthanum chloride. Lanthanum chloride was used at a 2% concentration (2 g/100 ml) in hydrophilic ointment base, USP, and the lanthanum was incorporated in the ointment at the time of exposure. The results of the patch test were read at 72 hours, and a photograph was taken. In the photograph, position number 1 shows the results of exposure to formaldehyde plus lanthanum, position number 2 shows response to formaldehyde with the ointment with the ointment base alone, and number 3 shows exposure to formaldehyde in water. There was a very slight decrease of inflammation due to the presence of the ointment base itself. This slight decrease as a result of the use the emollient only is a well known phenomenon. What is significant is that in the presence of lanthanum the inflammation was almost totally abolished. The effect of the lanthanum is clearly much greater than that of the ointment base alone.

EXAMPLE 6

Transfer of $La^{3+}$-induced suppression of hypersensitivity by transfer of spleen cells

Methods

Inbred mice of the strain AB ($H-2^k$) reared in the breeding colony of the Humboldt University Berlin were used. The mice were fed with water and standard pellets ad libitum. During all procedures (sensitization, challenge, measurement) the animals were anesthetized by an intraperitoneal injection of hexobarbital sodium salt. The number of animals per experimental group (n) is presented.

The mice were anesthesized in an area of 2.0×2.0 cm on their abdomen, abdominal skin was shaved with a blade, and a 20 microliters of a 0.5% solution of 2,4-dinitro-1-fluorobenzene (DNFB) (Serva, Heidelberg, F.R.G.) in acetone were applied to this site. This procedure was repeated one day later.

The challenge reaction was induced 5 days after the first sensitization by an application of 0.2% DNFB in acetone on the dorsal surfaces of both ears. The ear thickness was measured before and 24 hours after challenge using an engineers micrometer (Peacock, Japan).

10 g $LaCl_3 \times 7H_2O$ (Laborchemie Apolda, G.D.R.) was dissolved in 10 ml water and incorporated into unguentum alcoholum lanae aquosum. The previously shaved sensitization site on the abdominal skin of the mice was treated at the days numbered −1, 0, and +1 with this ointment. At the days 0 and +1, when contact sensitization with DNFB was performed, the ointment was applied on hour after sensitization, so that the penetration of the DNFB was not influenced by the ointment.

The spleens from mice treated with lanthanum and control animals were removed and homogenized by gently pressing the tissue through a steel mesh. The cell were suspended in RPMI 1640 medium (SIFIN, Berlin, G.D.R.) and were washed three times by centrifugation at 300 g for 10 minutes and resuspended. The treatment with monoclonal antibodies (mab) was performed by incubating the cells for 20 minutes with the L3T4 mab (clone GK 1.5, ATCC, Rockville, USA) or the anti-Lyt 2 mab (clone 53-6, ATCC, Rockville, USA) in a final dilution of 1:50. Thereafter the cells were washed 2 times and incubated for 20 minutes at 4° C. with a rat anti-mouse Ig mab (ATCC, Rockville, USA). The cells were washed 2 times and incubated for 30 minutes at 37° C. with normal rabbit serum, diluted 1:5 as a source of complement. The serum used was not toxic to the cells. Thereafter the cells were washed 2 times and $10^8$ viable cells were injected intravenously into native syngeneic mice.

Other groups of mice were sensitized by injection 50 microliters of ovalbumin (Serva, Heidelberg, F.R.G.) emulsified in 20 microliters of complete Freund's adjuvant (Difco laboratories, Detroit, U.S.A.) subcutaneously into the base of the tail. Eight days later the challenge was performed by injection 20 microliters of a 20% solution of heat-aggregated ovalbumin in saline. One day later foodpad swelling was measured.

The non-parametric Mann-Whitney test was used.

Results

To study whether the reduced DNFB reactivity after topical application of $LaCl_3$ is due to the development of suppressor cells, $10^8$ spleen cells from such hyporeactive mice were transferred to syngeneic untreated recipients, which were sensitized with DNFB immediately thereafter and challenged 5 days later. Table 2 shows that spleen cells of mice which were sensitized with DNFB after topical $LaCl_3$ treatment transferred the hyporesponsiveness to DNFB to native syngeneic recipients. Cells of untreated mice of DNFB sensitized mice caused no suppression in the recipients.

TABLE 2

Transfer of hyporesponsiveness to native syngeneic recipients by spleen cells of mice sensitized with DNFB on $LaCl_3$ treated skin[1].

| Group Treatment of the cell donor | Ear thickness ($10^{-2}$ mm ± SD) | % Suppression | n | $p^2$ |
|---|---|---|---|---|
| 1. no cell transfer | 46 ± 4.8 | — | 75 | — |
| 2. no donor treatment | 49 ± 2.0 | none | 7 | NS |
| 3. DNFB sensitization on normal skin | 50 ± 2.4 | none | 7 | NS |
| 4. DNFB sensitization | 29 ± 2.4 | 88 | 7 | 0.01 |

TABLE 2-continued

Transfer of hyporesponsiveness to native syngeneic recipients by spleen cells of mice sensitized with DNFB on LaCl$_3$ treated skin[1].

| Group Treatment of the cell donor | Ear thickness ($10^{-2}$ mm ± SD) | % Suppression | n | p[2] |
|---|---|---|---|---|
| on LaCl$_3$ treated skin | | | | |
| 5. DNFB sensitization on sham treated skin[3] | 47 ± 3.1 | none | 7 | NS |

[1]Mice were treated on a shaved abdominal skin site with an ointment containing 10% LaCl$_3$ at days −1, 0, and +1, and sensitized on the same skin site with DNFB at days 0 and +1. Seven days later spleen cells of these mice were transferred to native syngeneic recipients, which were immunized with DNFB thereafter. Five days later the ear swelling response of the recipients after challenge with DNFB was measured.
[2]Statistical difference to control group (1). NS = Not significantly different.
[3]Skin treatment with the ointment base alone (unguentum alcoholum lanae aquosum).

To investigate the phenotype of this suppressor cell, spleen cells were harvested from mice which were previously sensitized with DNFB on LaCl$_3$ pretreated skin. The cells were incubated in vitro with monoclonal antibodies against CD4 (L3T4) or CD8 (anti-lyt 2 mab) T cell determinants and complement. Thereafter the cells were washed 2 times and injected into untreated syngeneic recipients. Table 3 shows that only the mab against CD8 but not CD4 determinants abolished the suppressive activity of the cells. This shows that a splenic CD4-CD8+ suppressor T cell population is induced in LaCl$_3$-treated DNFB-sensitized mice.

TABLE 3

Phenotype of the Suppressor Cells[4]

| Group Treatment of the cell donor | Ear thickness ($10^{-2}$ mm ± SD) | % Suppression | n | p[5] |
|---|---|---|---|---|
| 1. no cell transfer | 50 ± 4.2 | 0 | 5 | — |
| 2. no treatment | 28 ± 2.1 | 100 | 5 | 0.01 |
| 3. anti CD4 mab | 33 ± 3.7 | 82 | 5 | NS |
| 4. anti CD8 mab | 50 ± 2.9 | 100 | 5 | NS |
| 5. Sham treatment[6] | 31 ± 2.6 | 14 | 5 | 0.01 |

[4]Mice were treated on a shaved abdominal skin site with an ointment containing 10% LaCl$_3$ at days −1, 0, and +1, and sensitized with DNFB at days 0 and +1. Seven days later spleen cells were harvested, treated in vitro, with mabs and complement, washed and transferred to native recipients, which were immunized with DNFB thereafter. The recipients' ear swelling response after challenge with DNFB was measured.
[5]Statistical difference to control group (1). NS = Not significantly different.
[6]Treatment with complement alone.

To test the antigenic specificity of the suppressor cell, spleen cells of mice sensitized with DNFB on LaCl$_3$-treated skin were transferred to native syngeneic recipients, which were immunized thereafter with an unrelated antigen (ovalbumin) which evokes the same type of immune response (delayed hypersensitivity). Table 4 shows that the footpad swelling response of the recipients to ovalbumin was not affected by the transferred cells. This demonstrates that that induced suppressor cells are antigenically specific.

TABLE 4

Antigenic specificity of the suppressor cells[7]

| Group Treatment of the cell donor | Ear thickness ($10^{-2}$ mm ± SD) | n | p[8] |
|---|---|---|---|
| 1. no cell transfer | .68 ± .12 | 8 | — |
| 2. no pretreatment | .64 ± .12 | 8 | NS |
| 3. DNFB sensitization on normal skin | .84 ± .11 | 8 | NS |
| 4. DNFB sensitization on | .68 ± .09 | 8 | NS |

TABLE 4-continued

Antigenic specificity of the suppressor cells[7]

| Group Treatment of the cell donor | Ear thickness ($10^{-2}$ mm ± SD) | n | p[8] |
|---|---|---|---|
| LaCl$_3$ treated skin | | | |

[7]Mice were treated on a shaved abdominal skin site with an ointment containing 10% LaCl$_3$ at days −1, 0, and +1, and sensitized with DNFB at days 0 and +1. Seven days later spleen cells were transferred to syngeneic untreated recipients, which were immunized with ovalbumin thereafter. Footpad swelling of recipients after challenge with same antigen was measured.
[8]Statistical difference to control group (1). NS = Not significantly different.

EXAMPLE 7

To further demonstrate the effectiveness of lanthanum in the suppression of dermatitis evoked by exposure to allergens in patients with known sensitivity, the following experiment has been performed. Seven patients with known contact allergic dermatitis were recruited. One had hypersensitivity to nickel, four of these individuals had allergies against formaldehyde, and two had known allergies against chromium sulfate. Patch tests were performed on the flexor surface of the forearm, and they are reported in Table 5. Three patch test were applied in each individual. Patient number 1 was exposed to nickel sulfate (5% weight per volume) in hydrophilic ointment base USP. "Results" refers to the amount of erythema in the patch test sites at 48 hours, judged on a scale of 0–3+, where 3+ represents maximum erythema and inflammation.

TABLE 5

| Patch Number | Treatment | Results @ 48 Hours |
|---|---|---|
| 1 | NiSO$_4$ (5% w/v, total 0.45 mg) LaCl$_3$ (5% w/v) Hydrophilic Ointment Base | 1+ |
| 2. | NiSO$_4$ (5% w/v, total 0.45 mg) LaCl$_3$ (2.5% w/v) Hydrophilic Ointment Base | 2+ |
| 3. | NiSO$_4$ (5% w/v, total 0.45 mg) No LaCl$_3$ Hydrophilic Ointment Base | 3+ |
| 1. | Formaldehyde (5% w/v, total 0.45 mg) LaCl$_3$ (5% w/v) | 1+ (4/4 patients) |
| 2. | Formaldehyde (5% w/v, total 0.45 mg) LaCl$_3$ (2.5% w/v) | 2+ (4/4 patients) |
| 3. | Formaldehyde (5% w/v, total 0.45 mg) No. LaCl$_3$ | 3+ (4/4 patients) |
| 1. | CrSO$_4$ (5% w/v, 0.45 mg) LaCl$_3$ (5% w/v) | 1+ (2/2 patients) |
| 2. | CrSO$_4$ (5% w/v, 0.45 mg) LaCl$_3$ (2.5% w/v) | 2+ (2/2 patients) |
| 3. | CrSO$_4$ (5% w/v, total 0.45 mg) No LaCl$_3$ | 3+ (2/2 patients) |

In seven patients tested to date, lanthanum chloride showed a dose dependent effect in suppression of inflammation upon challenge to known sensitizing agents. In all individuals there was a significant suppression of inflammation in the presence of 5% lanthanum chloride incorporated at the time of exposure to known allergen. This provides significant preliminary data that, in humans, the elicitation phase of allergic contact dermatitis (response to challenge) can be down regulated by the application of topical lanthanum chloride.

EXAMPLE 8

To date, eight patterns with endogenous eczema (atopic dermatitis) have been treated with topical lanthanides. In three individuals, atopic dermatitis affected the majority of the body surface. These three patients were treated with a single total body application of lanthanum chloride (5% in hydrophilic ointment base). Blood levels of lanthanum were measured by atomic absorption spectroscopy, over a period of ½ to 24 hours after the single application. Blood levels of lanthanum are displayed in the table below.

| Time after application (in hours) | Blood Concentration of $La^{+3}$ $La^{+3}$ [ug/ml] ± SD |
|---|---|
| 0.5 | 0.004 ± 0.0028 |
| 1 | 0.0123 ± 0.0023 |
| 2 | 0.01216 ± 0.0030 |
| 4 | 0.0309 ± 0.0022 |
| 12 | 0.014 ± 0.0016 |
| 24 | 0.011 ± 0.0036 |

This data establishes that there is some systemic absorption of the lanthanum after topical application to the whole body. The peak blood levels appears at approximately 4 hours after administration, and in these individuals the level was 0.0309 microgram/ml of blood. This level is well below those levels known to produce toxicity in animals and humans. This also provides evidence that the lanthanum chloride does penetrate the stratum corneum of the epidermis, and at least a small amount manages to get through the epidermis and into the cutaneous circulation where it is then transported throughout the blood stream.

EXAMPLE 9

Five patients with atopic dermatitis affecting the hands were treated with topical lanthanides. In this protocol individuals were dispensed a 5% lanthanum chloride ointment and were instructed to use a thin film on the hands twice daily immediately before work and immediately upon returning home from work. These individuals did so for a period of 1-3 months. During that period of time, they experienced significant improvement of their hand dermatitis and a decrease in fissuring, oozing, and puritis. This indicates that topical lanthanides in humans can down regulate endogenous eczema that may be precipitated or aggravated by non-specific stimuli such as irritants and trauma.

We claim:

1. A method for the treatment of cutaneous delayed-type hypersensitivity (DTH) in an animal comprising administering to said animal a therapeutically effective amount of a calcium flux inhibiting compound selected from the group consisting of lanthanide ions which are calcium analogs and organic calcium channel blockers.

2. The method of claim 1 wherein the calcium flux inhibiting compound is a lanthanide ion.

3. The method of claim 2 wherein the lanthanide is $La^{+3}$.

4. The method of claim 1, 2, or 3 wherein the calcium flux inhibiting compound is administered prior to exposure of the animal to a contact antigen so as to suppress sensitization of said animal to said antigen.

5. The method of claim 1, 2, or 3 wherein the calcium flux inhibiting compound is administered to the animal after the animal has been sensitized to a contact antigen.

6. The method of claim 1, 2 or 3 wherein the calcium flux inhibitor is administered by topical application.

7. The method of claim 6 wherein the calcium flux inhibitor is applied in a pharmaceutical composition comprising a carrier acceptable for topical application.

8. The method of claim 7 wherein the composition additionally comprises a penetration enhancing material whereby penetration into the skin by the calcium flux inhibitor is promoted.

9. The method of claim 7 wherein the calcium flux inhibitor is present in the composition at from about 0.001% to about 30% by weight.

10. The method of claim 7 wherein the calcium flux inhibitor is present in the composition at from about 0.01% to about 20% by weight.

11. The method of claim 7 wherein the calcium flux inhibitor is present in the the composition at from about 0.1% to about 10% by weight.

12. A method for the treatment of atopic eczema comprising topically applying a calcium flux inhibitor selected from the group consisting of lanthanide ions which are calcium analogs and organic calcium channel blockers to an animal having atopic eczema in an amount sufficient to reduce the inflammation caused by atopic eczema.

13. The method of claim 12 wherein the calcium flux inhibitor is a lanthanide ion.

14. The method of claim 13 wherein the lanthanide ion is $La^{+3}$.

15. The method of claim 12, 13 or 14 wherein the calcium flux inhibitor is applied in a pharmaceutical composition comprising a carrier acceptable for topical application.

16. The method of claim 15 wherein the composition also comprises a penetration enhancing material whereby penetration into the skin by the calcium flux inhibitor is promoted.

17. The method of claim 15 wherein the calcium flux inhibitor is present in the composition at from about 0.001% to about 30% by weight.

18. The method of claim 15 where the calcium flux inhibitor is present in the composition at from about 0.01% to about 20% by weight.

19. The method of claim 15 wherein the calcium flux inhibitor is present in the composition at from about 0.01% to about 10% by weight.

20. A pharmaceutical composition for the treatment of cutaneous delayed-type hypersensitivity or for the treatment of atopic eczema comprising a therapeutically effective amount of a calcium flux inhibitor selected from the group consisting of lanthanide ions which are calcium analogs and organic calcium channel blockers, a penetration enhancing material whereby penetration into the skin by the calcium flux inhibitor is promoted, and a carrier which is pharmaceutically acceptable for topical application.

21. The composition of claim 20 wherein the calcium flux inhibitor is a lanthanide ion.

22. The composition of claim 21 wherein the lanthanide ion is $La^{+3}$.

23. The composition of claim 20 wherein the calcium flux inhibitor is an organic calcium channel blocker.

24. The composition of claims 20, 21, or 22 wherein the carrier is selected from the group consisting of hydrophilic ointment USP, emulsion ointment base (water in oil) USP, hydrophilic petrolatum USP, hydrous wool fat-lanolin USP, white wax-bleached bees wax USP, glycerin, water/propylene glycol 50%/50%, and pure aqueous solution.

25. The composition of claims 20, 21, or 22 wherein the calcium flux inhibitor is present at from about 0.001% to about 30% by weight.

26. The composition of claims 20, 21 or 22 wherein the calcium flux inhibitor is present at from about 0.01% to about 20% by weight.

27. The composition of claims 20, 21 or 22 wherein the calcium flux inhibitor is present at from about 0.1% to about 10% by weight.

* * * * *

UNITED STATES PATENT AND TRADEMARK OFFICE
CERTIFICATE OF CORRECTION

PATENT NO. : 5,202,130
DATED : April 13, 1993
INVENTOR(S) : Grant ANHALT & Wolfgang DIEZEL It is certified that error appears in the above-indentified patent and that said Letters Patent is hereby corrected as shown below:

On the title page, under item [19], "Grant et al" should be replaced with --Anhalt et al--; and item [75], "Anhalt Grant" should be replaced with --Grant Anhalt-- and "Diezel Wolfgang" should be replaced with --Wolfgang Diezel--.

On page 2, the first 2 lines should be moved from the top of column 1 to the bottom of column 2.

Signed and Sealed this

Twenty-ninth Day of March, 1994

BRUCE LEHMAN

*Attest:*

*Attesting Officer*     *Commissioner of Patents and Trademarks*